United States Patent [19]

Hyman, Jr. et al.

[11] Patent Number: 5,572,314
[45] Date of Patent: Nov. 5, 1996

[54] BREWSTER ANGLE REFRACTOMETER

[76] Inventors: Mark Hyman, Jr., 1010 Memorial Dr., Cambridge, Mass. 02138; Cornelius S. Hurlbut, 1010 Waltham St., Lexington, Mass. 02173

[21] Appl. No.: 308,696

[22] Filed: Sep. 19, 1994

[51] Int. Cl.⁶ ............................................. G01N 21/41
[52] U.S. Cl. ............................ 356/128; 356/30; 356/369
[58] Field of Search ........................... 356/128, 129–134, 356/30, 31, 364, 369, 370; 250/225; 359/487, 488

[56] References Cited

U.S. PATENT DOCUMENTS

| | | | |
|---|---|---|---|
| 3,751,162 | 8/1973 | Long | 356/30 |
| 3,975,097 | 8/1976 | Minto | 356/30 |
| 4,012,141 | 3/1977 | Hanneman | 356/448 |
| 4,179,190 | 12/1979 | Friedman et al. | 359/487 |
| 4,210,401 | 7/1980 | Batten | 356/369 |
| 4,249,824 | 2/1981 | Wiederrich et al. | 356/153 |
| 4,368,982 | 1/1983 | Van Arnam et al. | 356/445 |

FOREIGN PATENT DOCUMENTS 0035306  2/1989  Japan ................................... 356/369

OTHER PUBLICATIONS

Read, P. G., "An Experimental Brewster–Angle Refractometer," J. Gemm. 16:537–541, 1979.
Read, P. G., "Further Development of the Brewster–Angle Refractometer," J. Gemm. 21:36–39, 1988.
Yu, R. M., "The Brewster Angle Refractometer," Gems and Gemology, 245–247, Winter, 1979.

Primary Examiner—Hoa Q. Pham
Attorney, Agent, or Firm—Fish & Richardson P.C.

[57] ABSTRACT

A Brewster angle refractometer, based on the principal that reflectivity of light polarized parallel to the plane of incidence is minimized at the Brewster angle, is used to determine the refractive index of a material. The refractometer has a precision mechanical drive arrangement for precisely determining the refractive index over a range of 1.4 to 3.0, with an accuracy of at least ±0.02.

14 Claims, 3 Drawing Sheets

BREWSTER ANGLE REFRACTOMETER

BACKGROUND OF THE INVENTION

This invention relates to Brewster angle refractometers intended for measuring the refractive indices of solids, particularly gemstones.

Refraction is the changing of the direction of an optical field passing obliquely from one material to another in which the speed of light is different. The refractive index ("n") of a material is a number indicating the ratio of the speed of light in a vacuum ("c") to the speed of light ("v") propagating through the particular material:

$$n = c/v \qquad (1)$$

Using optical methods, such as absorption or reflection spectroscopy, the refractive index of a material can be measured For instance, the reflectivity ("r", defined as the ratio of incident to reflected light) at the air/solid interface of a material is related to the refractive index using Fresnel's formula:

$$r = (n-1)^2/(n+1)^2 \qquad (2)$$

Thus, measurement of the intensity of incident and reflected light allows the refractive index to be determined. The use of this particular technique to identify gemstones is described in Long, U.S. Pat. No. 3,751,162, among others. Unfortunately, this method is complicated by the fact that the intensities of two optical fields, that is, the incident and reflected fields, must be determined in order to calculate n.

Alternatively, the manner in which a single beam of light at a specific polarization is reflected (and refracted) at an air/solid interface can be used to determine the refractive index of the solid. Specifically, for an incident optical field, there is a particular angle of incidence (relative to the normal vector of the surface), called the Brewster angle, which is related to the refractive index of a material. At this angle, the reflection coefficient of light polarized parallel to the plane of incidence (that is, the plane containing the incident and reflected fields) is zero. Thus, if the incident light is non-polarized and impinges on the material at the Brewster angle, the light reflected from the solid will be polarized in the plane perpendicular to the plane of incidence. If the incident light is polarized parallel to the plane of incidence, the intensity of the reflected light will be theoretically zero at the Brewster angle.

Determination of the refractive index can be used to identify a particular material. For example, at 589 nm, the refractive index of diamond is 2.42, whereas cubic zirconia, a manufactured diamond simulant, has a refractive index of about 2.18. Accurate determination of the refractive index can be used to differentiate one gem from another, and allows imitation materials to be distinguished from gemstones.

SUMMARY OF THE INVENTION

The present invention allows for rapid determination of the refractive index of a material by carefully varying the angle of incidence of parallel-polarized light, and detecting the intensity of the reflected field. A null in the reflected signal indicates the Brewster angle, allowing the refractive index of the material to be determined.

In one aspect of the invention, a Brewster angle refractometer utilizing the angle-dependent reflective properties of a material is used to determine the material refractive index.

In preferred embodiments, the material has a refractive index between 1.4 and 3.0, and is preferably a gemstone, such as diamond.

The refractometer contains a light source providing an incident optical beam for illuminating a surface of the material at an angle relative to the normal vector of the surface. The incident optical beam from the light source is polarized in a direction substantially parallel to a plane containing the incident optical beam and its reflection from the surface of the material. In preferred embodiments, the wavelength of light produced from the light source is not strongly absorbed by the material, and is preferably between 590–800 nm. Preferably, the light source is an LED or a diode laser. In addition, the refractometer contains a rectangular aperture for transmitting the incident and reflected beams, with the aperture being elongated and having beveled ends to allow transmission of beams having high angles of incidence.

The refractometer of the present invention also contains a photosensitive detector for receiving the reflected beam, and for generating a light-induced electric signal which varies according to the intensity of the beam. In preferred embodiments, the photosensitive detector is a photodiode, preferably one which has a spectral response (that is, the spectral region over which the photodiode generates photocurrent) substantially matched to the emission spectrum of the light source. In especially preferred embodiments, the spectral response of the photodiode lies substantially between 590–800 nm. In other preferred embodiments, the photodiode is mounted in a fixed position and orientation perpendicular to the mean angle of the reflected beam.

The Brewster angle refractometer also contains a gear for varying the angle of the incident optical beam, with the gear being connected to the light source such that the incident optical beam is pivoted about a point on the surface of the material during rotation of the gear, thereby resulting in variation in the angle of the incident optical beam. Additionally, a worm gear is engaged with the gear so that when rotated, the worm gear results in rotation of the gear. In preferred embodiments, this gearing allows the angle separating the surface normal vector and the incident beam to be varied between 54° and 72°; preferably, the angle can be adjusted with a resolution of ±0.15°.

In addition, an electronic circuit is included in the refractometer for powering the light source and photosensitive detector, and for amplifying the light-induced signal from the detector. A meter or numerical display is connected to the electronic circuit to allow determination of the null in the light-induced signal which occurs when the angle of the polarized, incident optical beam is substantially equivalent to the Brewster angle. In especially preferred embodiments, the Brewster angle refractometer includes a knob for rotating the worm gear, thus allowing adjustment of the angle of the incident optical beam. The knob includes calibrated markings which allow a direct readout of the refractive index of the material when the null in the light-induced signal is determined.

BRIEF DESCRIPTION OF THE DRAWINGS

The drawings will first be briefly described.

DESCRIPTION OF THE PREFERRED EMBODIMENTS

Figure 1A:
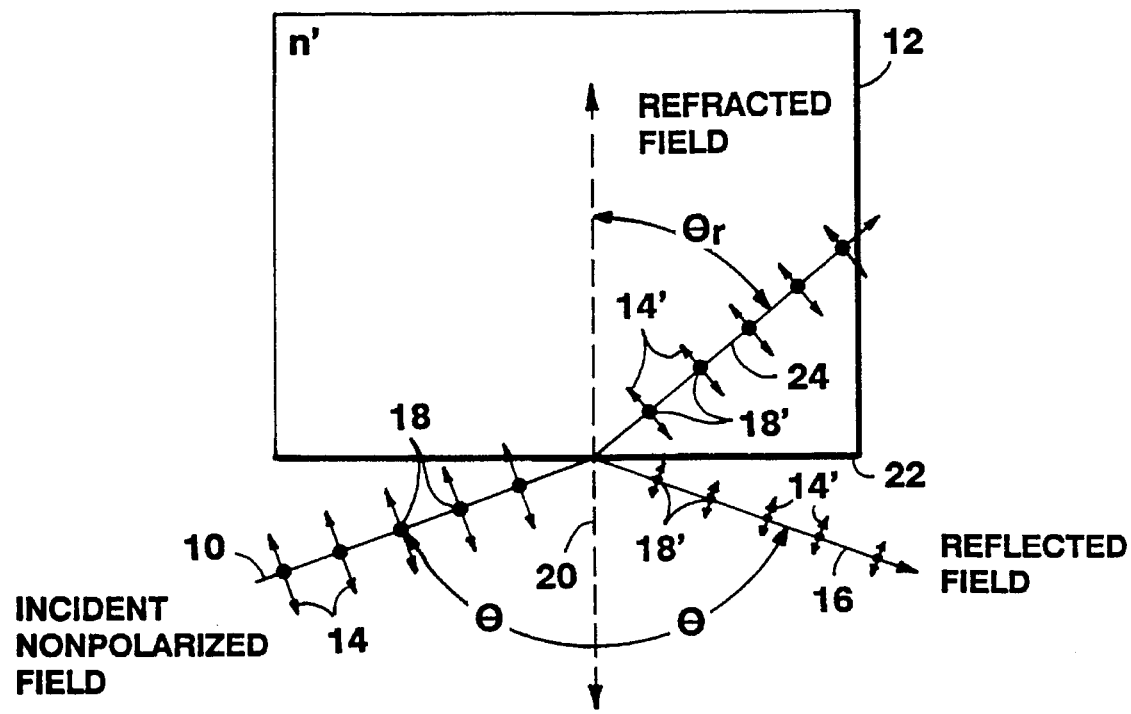
FIG. 1A is a schematic showing the reflected and refracted optical fields when the angle of the incident optical field is greater than the Brewster angle.
Figure 1B:
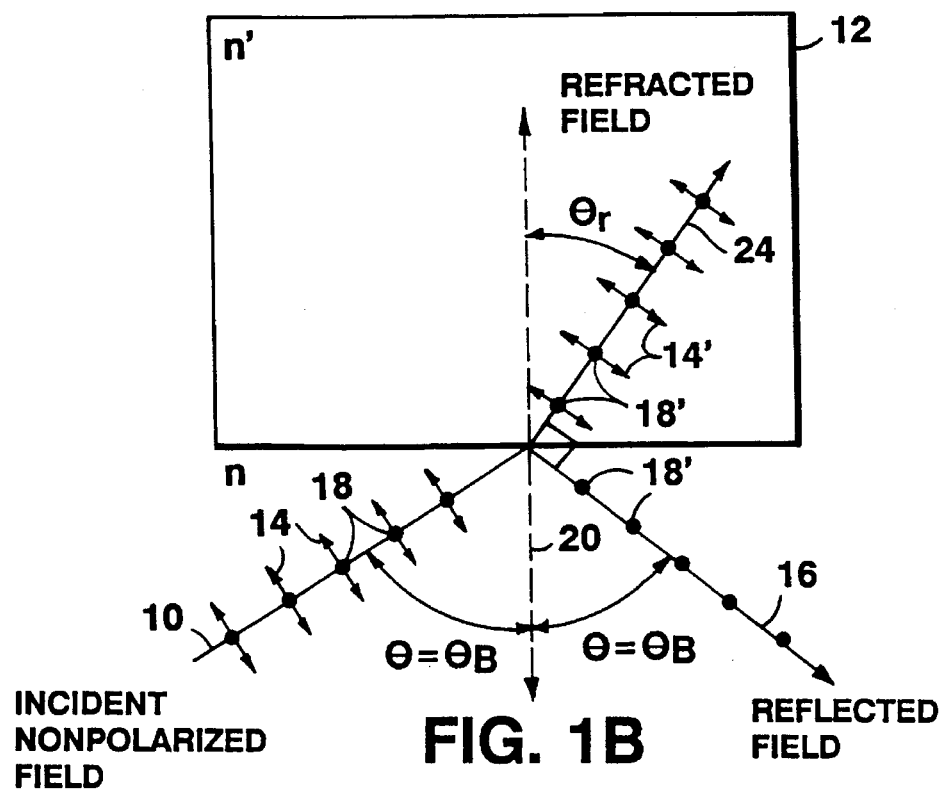
Fig. 1B is a schematic showing the reflected and refracted optical fields when the angle of the incident optical field is equal to the Brewster angle.

Referring first to FIGS. 1A and 1B, the principle of polarization-dependent reflection used to advantage in the present invention is illustrated schematically using an incident optical field 10 impinging on a sample 12 having a refractive index of n'. The incident field 10 is nonpolarized, and can be resolved into polarization components which are parallel 14 and perpendicular 18 to the plane of incidence.

The angle of incidence, $\Theta$, is defined as the angle separating the incident field 10 and a vector 20 normal to the plane of an air/sample interface 22. Referring now to FIG. 1A, an incident field 10 impinging the air/sample interface 22 will result in a reflected field 16, and a refracted field 24 which propagates through the sample 12 at an angle $\Theta_r$ relative to the normal vector 20. When the angle of incidence is greater than the Brewster angle ($\Theta_B$), both the reflected field 16 and the refracted field 24 will have polarization components parallel 14' and perpendicular 18' to the plane of incidence; the magnitudes of these components depend on $\Theta$.

Referring to FIG. 1B, when the angle of incidence is equal to $\Theta_B$, the reflection coefficient for the component 14' parallel to the plane of incidence is zero, and only the perpendicular polarization component 18 is reflected. Thus, for nonpolarized light incident at $\Theta_B$, the reflected field 16 is polarized. If the incident field 10 is polarized exclusively parallel to the plane of incidence, as is the case for the most preferred embodiment of the invention, the intensity of the reflected field will be zeroed at $\Theta_B$, and the refracted beam 24 will be polarized parallel to the plane of incidence.

Brewster found that at $\Theta_B$ the reflected and refracted beams 16, 24 are at right angles, that is, $$\Theta_B + \Theta_r = 90°. \tag{3}$$

From the law of refraction, $$n_{air} \sin \Theta_B = n' \sin \Theta_r \tag{4}$$

thus, combination of equations (3) and (4) leads to $$\tan \Theta_B = n'/n_{air}. \tag{5}$$

$\Theta_B$ therefore depends on the refractive index of the material in a well-defined, non-linear manner, and measurement of $\Theta_B$ using parallel polarized light allows determination of the refractive index.

Figure 2:
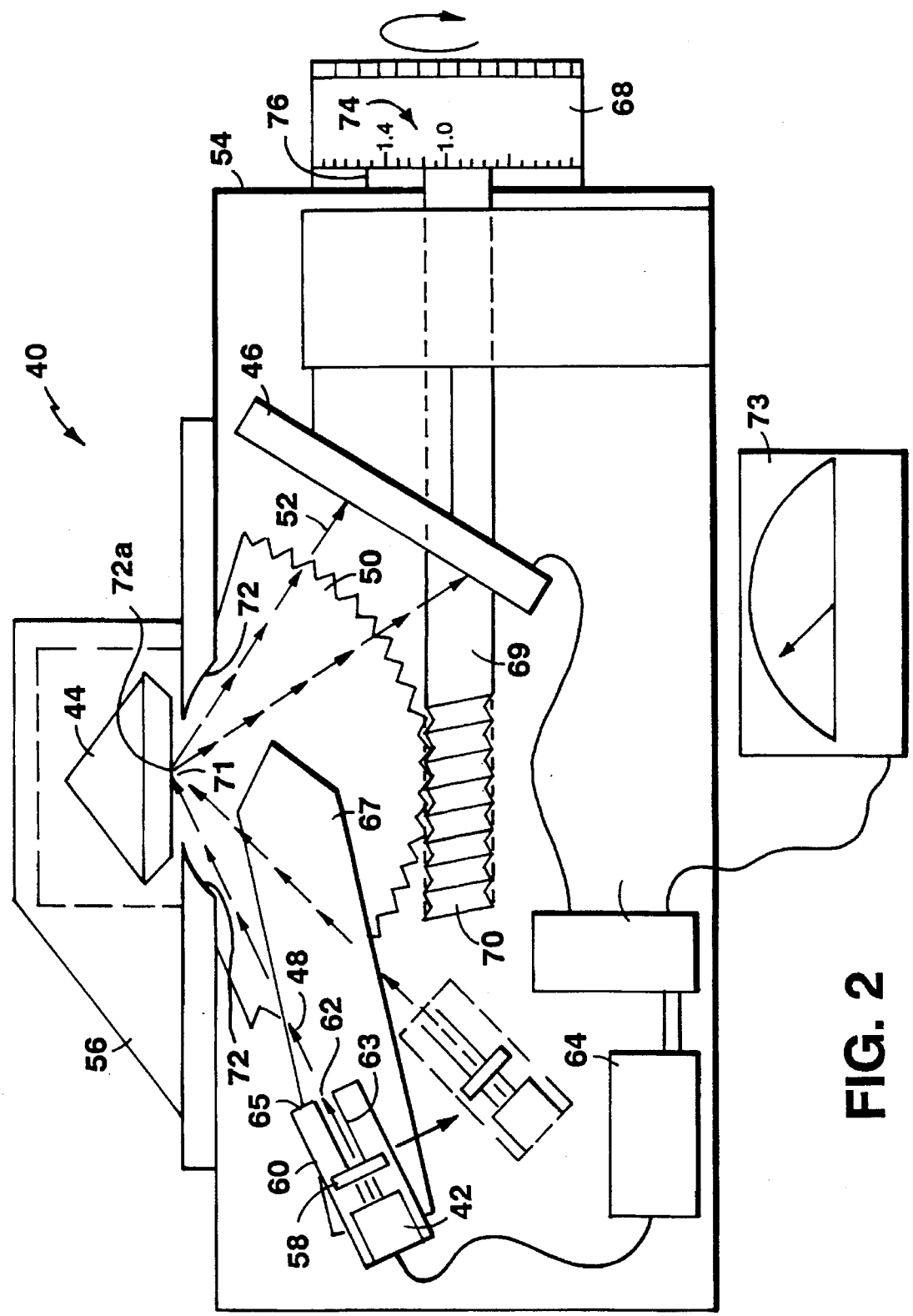
FIG. 2 is a cut-away side view of the Brewster angle refractometer in accordance with a preferred embodiment of the invention.

Referring now to FIG. 2, the Brewster angle refractometer 40 the present invention uses a light source 42 to illuminate the surface of a sample 44. For accurate measurements, the material is preferably of high optical quality, meaning that the surface is polished flat and does not have significant local variations in the refractive index. In addition, the material should not have strong optical absorption at the emission wavelength of the light source. Gemstone materials, such as diamonds, satisfy these criteria; their refractive indices can therefore be accurately measured with the present invention.

In order to maximize the measuring sensitivity of the refractometer 40, all optical and mechanical components are sealed in a light-tight box 54, which is colored matte black on the inner surface so that stray internal reflections are absorbed. In addition, during measurement, the sample 44 is covered by a shroud 56, which may be hinged on one end to the upper surface of the light-tight box 54 to allow easy insertion of the sample 44 to be measured.

In the illustrated embodiment, a housing 60 containing the light source 42 is connected to a gear 50 using a bridging section 67. The angle between an incident optical field 48 and the sample 44 is varied by rotating a knob 68 attached to a gear shaft 69, which is connected to a worm gear 70. Rotating the knob 68 turns the gear 50, resulting in angular variation in the incident beam 48 from the light source 42. In the illustrated embodiment, the angle of the incident beam 48 relative to the normal vector can be varied from about 54° to 72°, a range which covers the Brewster angles of most gemstone materials. At all angles, the incident field passes through an elongated rectangular aperture 71, which has beveled ends 72 along the plane of the incident and reflected fields. The beveled ends 72 allow greater optical throughput for the incident and reflected fields, while keeping the amount of stray light entering the box to a minimum; in preferred embodiments, the beveled ends 72 are cut using a circular saw blade.

To ensure the accuracy of the refractive index measurement, the light source 42 is mounted so that when rotated, the pivoting point is coincident with a point 72a lying on the surface of the sample 44 being measured. Thus, although rotation results in a change in the angle of incidence, the illuminated spot on the surface remains fixed. In addition, the gear 50 and worm gear 70 are precision machined to eliminate backlash, and can be finely adjusted to allow the angle of the incident beam 48 to be precisely varied over the entire angular range. In the present invention, a resolution of about 0.15° can be achieved using a worm gear having approximately 7 threads/cm. By providing a highly accurate gearing apparatus, the present invention allows precise determination of $\Theta_B$ for a given material, thus allowing the refractive index to be accurately measured.

During operation, the incident optical field 48 is generated using a light source 42 and is polarized along the direction parallel to the plane of incidence using a polarizing filter 58. Alternatively, nonpolarized light may be used to illuminate the sample, and the polarization filter is placed directly in front of the optical detector 46. In preferred embodiments, the light source 42 is a light emitting diode ("LED"), such as the MT4000-UR LED, (Marktech, Inc., Latham, N.Y. 12110) which has a peak emission wavelength at 660 nm, and a spectral bandwidth of about 25 nm; other LEDs having other emission wavelengths may also be used. In order to maximize the accuracy of the refractive index measurement, the emitted beam is polarized so that the ratio of parallel to perpendicular polarization components is greater than about 100:1. This results in a well-defined null in the intensity of the reflected field 52 when the incident field 48 is at angle $\Theta_B$ with respect to the surface of the sample 44 being illuminated.

Both the light source 42 and the polarizing filter 58 are sealed inside the housing 60 containing a tube 63 which serves as a collimator for the emerging beam. Once emitted and polarized, the incident beam 48 propagates through an aperture 62 having a diameter of 0.050" located at the end of the tube 63, where it is used to illuminate the sample 44.

Typically, for materials such as gemstones, optical wavelengths greater than about 500 nm are not strongly absorbed; LEDs emitting in the yellow and red (590–700 nm) or near infrared (700–800 nm) spectral region may therefore be used in accordance with the invention. In preferred embodiments, an optical intensity of less than about 5 mW is used to irradiate the material. Other light sources having suitable emission wavelengths, spectral bandwidths and power outputs, such as laser diodes, may also be used with the invention. For all light sources, a battery source 64 supplying a voltage between about 4.5–6.0 V, at a current of about 100 mA, is used for powering purposes.

Light reflected from the sample 44 is measured with the optical detector 46, which preferably has a spectral response matched to the peak emission wavelength and spectral bandwidth of the light source 42. In preferred embodiments, a silicon photodiode, such as the Hamamatsu S1227 diode, may be used. The sensitivity of this particular photodiode peaks at about 700 nm, and the spectral response extends from 320 nm to about 800 nm. Typically, in order to achieve adequate sensitivity, multiple gain settings are provided by a circuit 66 so that the light-induced signal from the photodiode can be amplified, allowing accurate measurement of the signal null.

During measurement of the refractive index, the optical detector 46 is held fixed, while the angle of the incident optical field 48 relative to the sample 44 is varied. To ensure that the reflected field 52 is detected over a full range of angles, a photodiode having a large detection area (for example, 1 cm$^2$ for the S1227 photodiode) is preferred. In addition, the distance separating the detector 46 and the illuminated portion of the sample is minimized; in preferred embodiments of the present invention, this distance, chosen to be about 1.5 cm, allows reflected fields emerging at angles between 54° and 72° to be measured by the detector 46.

During a typical measurement operation, the sample 44 is centered over the aperture 71 and covered with the shroud 56. The knob 68 is then slowly rotated while the amplitude of a measured DC signal, indicated by a readout element 73, is observed. Typically, the gain on the photodiode is set so that the reflected signal is in the linear response region of the photodiode, and so the readout element 73 is not saturated. The resistance of the photodiode increases with the decreasing intensity of received reflected light. This results in a decrease in photocurrent, and a minimized reading on the readout element 73, when the angle separating the incident optical field and the normal surface vector is $\Theta_B$.

The refractive index of the material is then determined by comparing the previously determined calibrated markings 74 on the knob 68 with a fixed line 76. Due to the nonlinear dependence of the refractive index on $\Theta_B$ (see, for example, equation 5), the calibrated markings 74, which represent equal step changes in the measured index of refraction, are not evenly spaced, with the spacing between markings at higher refractive indices being decreased. In general, when calibrated with known materials, the instrument of the invention has the capability to resolve refractive indices with an accuracy of about ±0.02. Using the method and apparatus described herein, accurate measurements can be easily made, allowing, for example, real and imitation gemstones to be rapidly distinguished.

Figure 3:
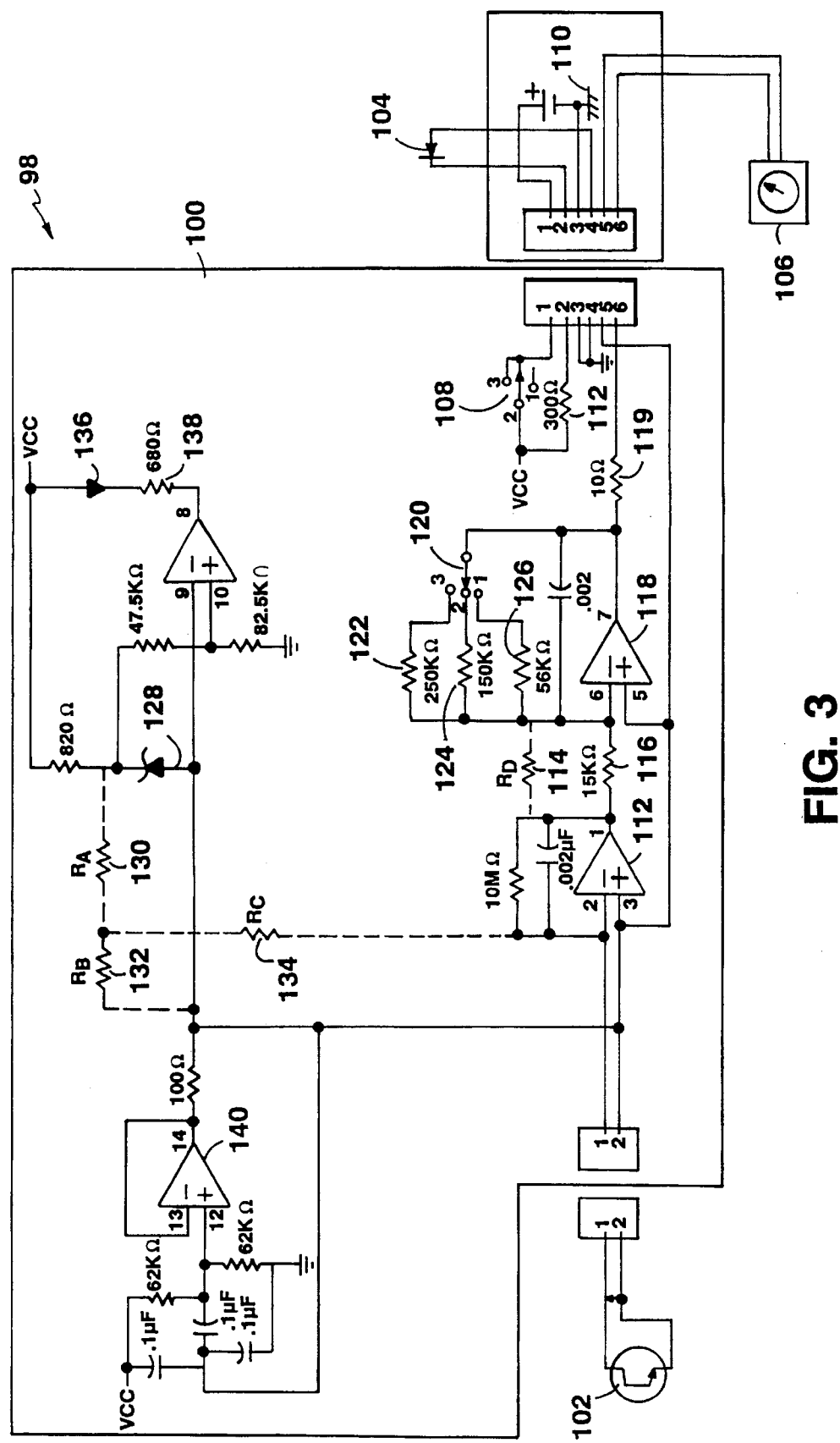
FIG. 3 is an electronic circuit diagram for the light source and detector used in the Brewster angle refractometer in accordance with a preferred embodiment of the invention.

Referring now to FIG. 3, the electronic circuitry 98 of the invention, contained within the light-tight box, includes a circuit board 100, a photodiode 102, an LED 104, and 4 AA-cell batteries connected in series to provide a 6 V potential difference to power the circuit. An analog readout element 106 is mounted on the light-tight box to allow the movement of the readout element's needle resulting from the light-induced signal from the photodiode 102 to be viewed.

In the circuit, the LED 104 is powered by completing the circuit with an on/off switch 108; this allows the diode to be biased with a potential difference of 6 V relative to a chassis ground 110. A resistor 112 is placed in series with the LED 104 to limit the current flow through this component.

Light reflected by the sample is detected with a photodiode 102, which is connected to an operational amplifier 112 used to amplify the induced photocurrent. All amplifiers in circuit board 100 are contained in a single integrated circuit (Texas Instruments, model TLC27M4ACN) in which voltage is applied to the "4" pin and the "11" pin is connected to a low potential. An optional resistor 114 may be connected in parallel to a resistor 116 in order to increase the photocurrent amplification, depending upon the output range of the photodiode. Following the first stage of current-to-voltage amplification, the output from amplifier 112 is fed into a second amplifier 118, whose output is connected through a switch 120 to one of three resistors 122, 124, 126, thus allowing three different amplification levels. The output of amplifier 118 is connected through a resistor 119 to the analog readout element 106, which is used to determine the null in the reflected light.

In order to offset any bias current introduced by the operational amplifiers contained on the integrated circuit, a 1.2 V Zener diode 128 is included in the circuit. This element provides a stable reference voltage and in conjunction with the three resistors 130, 132, 134 may be added to the circuit, as is well known in the circuit art, to further offset the effects of current which is not photogenerated.

Finally, an indicating LED 136 is provided in series with a resistor 138 to form a threshold circuit used to register a high (that is, greater than 4.16 V) powering voltage. A non-inverting amplifier 140 is used to generate a positive or negative voltage relative to an accurate ground for the circuit.

The foregoing descriptions of the preferred embodiments of the invention have been presented for purposes of illustration and description. They are not intended to be exhaustive or to limit the invention to the precise form disclosed. The embodiments chosen are described in order to best explain the principles of the invention.

What is claimed is:

1. A Brewster angle refractometer for determining the refractive index of a material, comprising:

a light source providing an incident optical beam for illuminating a surface of said material, said light source being attached to one end of a bridging section for positioning said light source and said incident optical beam at an adjustable angle relative to the normal vector of said surface, said incident optical beam having a polarized component in a direction substantially parallel to a plane containing said incident optical beam and a second reflected beam, a photosensitive detector for receiving said reflected beam, said detector generating a light-induced signal which varies according to the intensity of said reflected beam, a gear for varying said angle of said incident optical beam, said gear attached in a fixed relationship to said bridging section at an end opposite to said light source and configured such that said incident optical beam is pivoted about a point on said surface of said material during rotation of said gear, thereby varying said angle of said incident optical beam, a worm gear engaged with said gear such that when rotated, said worm gear rotates said gear, an electronic circuit for powering said light source and said photosensitive detector, and for electrically amplifying said light-induced signal from said photosensitive detector, a readout element connected to said electronic circuit for determination of a null in said light-induced signal, said null occurring when said angle of said incident optical beam is substantially equivalent to the Brewster angle for said material, and a calibrated knob attached directly to said worm gear, said knob comprising a set of calibrated markings correlating to the refractive index of the material such that when rotated, said knob pivots said bridging section to adjust the angle of said incident optical beam to determine mechanically the null in the light-induced signal, with a calibrated marking within said set corresponding to the refractive index of the material when the null in said light-induced signal is determined, thereby allowing determination of said refractive index of said material.

2. The Brewster angle refractometer of claim 1, wherein said material has a refractive index between 1.4 and 3.0.

3. The Brewster angle refractometer of claim 2, wherein said material is a gemstone.

4. The Brewster angle refractometer of claim 1, wherein said angle can be varied between 54° and 72° relative to said normal vector of said surface.

5. The Brewster angle refractometer of claim 4, wherein said angle can be varied with a resolution of less than ±0.15°.

6. The Brewster angle refractometer of claim 1, wherein light produced by said light source includes a wavelength which is not substantially absorbed by said material.

7. The Brewster angle refractometer of claim 6, wherein said wavelength of light is between 590–800 nm, inclusive.

8. The Brewster angle refractometer of claim 7, wherein said light source is an LED.

9. The Brewster angle refractometer of claims 7, wherein said light source is a diode laser.

10. The Brewster angle refractometer of claim 1, further comprising a rectangular aperture having beveled ends for transmitting said incident optical beam and said reflected beam.

11. The Brewster angle refractometer of claim 1, wherein said photosensitive detector is a photodiode.

12. The Brewster angle refractometer of claim 11, wherein said photodiode has a spectral response substantially matched to a wavelength produced by said light source.

13. The Brewster angle refractometer of claim 11, further comprising means for mounting said photodiode in a fixed position and orientation relative to said point about which said incident optical beam is pivoted.

14. The Brewster angle refractometer of claim 11, wherein said photodiode has a spectral response substantially between 590–800 nm, inclusive.

* * * * *